United States Patent [19]

Dutta

[11] Patent Number: 4,759,927

[45] Date of Patent: Jul. 26, 1988

[54] VACCINE AGAINST POTOMAC HORSE FEVER AND METHOD OF PREPARATION THEREFORE

[75] Inventor: Sukanta K. Dutta, Lanham, Md.

[73] Assignee: University of Maryland, College Park, Md.

[21] Appl. No.: 944,851

[22] Filed: Dec. 22, 1986

[51] Int. Cl.[4] .................. A61K 39/002; A61K 39/00; C12N 11/06

[52] U.S. Cl. ........................................ 424/88; 424/92; 435/7; 435/68; 435/177; 435/188; 435/803; 435/810; 530/806

[58] Field of Search ................. 424/88, 92; 425/7, 68, 425/803, 810; 530/806

[56] References Cited

U.S. PATENT DOCUMENTS 4,372,945  2/1983  Likhite ................................. 424/88

OTHER PUBLICATIONS

Robl, *Veterinary Medicine*, 49–58, (1985).
Holland et al., Science, 227, 522–524, (1985).
Dutta et al., Journal of Clinical Microbiology, 2, 265–269, (1985).

*Primary Examiner*—Howard E. Schain
*Attorney, Agent, or Firm*—Oblon, Fisher, Spivak, McClelland & Maier

[57] ABSTRACT

A vaccine against Potomac Horse Fever comprises a deactivated *E. risticii* as the active agent. The agent may be obtained through inoculation of a cell culture, followed through deactivation by exposure to b-propiolactone. The deactivated *E. risticii* is subsequently isolated and suspended in a pharmaceutically acceptable carrier. Considerable protection against infection is conferred. An assay is also prepared.

4 Claims, No Drawings

VACCINE AGAINST POTOMAC HORSE FEVER AND METHOD OF PREPARATION THEREFORE

BACKGROUND OF THE INVENTION

1. Field of the Invention:

This invention is directed to a vaccine for Potomac Horse Fever, effective in the prevention of occurrence of the disease in horses and related mammalian species. A method of preparing and administering the vaccine is also addressed.

2. Identification of the Disease and its Agent

In summer of 1979 a new equine disease was documented in this country, first appearing in Montgomery County, Md. In subsequent years, outbreaks of the disease, appearing in contagionfashion in certain instances, appeared from coast to coast, and in Canada. Although the symptoms of the disease are diverse, and associated with a large variety of equine diseases, repeated outbreaks under similar conditions, yielding similar results suggested a single causative agent responsible for the new disease.

The agent was finally identified and named in 1985, Holland et al, 227 Science, pages 522-524 (1985). In the Ehrlichia family, the agent has come to be designated *Ehrlichia risticii*, or *E. potomacensis*. Shortly thereafter, the identity of the agent was confirmed, and a relatively quick enzyme-linked immunosorbent assay (ELISA) to determine the presence of the agent which generates symptoms similar to many other diseases, was developed. Dutta et al, 22 Journal of Clinical Microbiology 2, pages 265-269 (1985).

Problems Involved In Treatment Of the Disease and Agent

Although ehrlichial organisms, and equine diseases caused thereby, are by no means unknown, Potomac Horse Fever (PHF) presents several particular problems in establishing a comprehensive, effective method of symptomatic and prophylactic treatment of the disease.

The disease is characterized by a marked variation in the presentation and severity of clinical symptoms. A wide variety of intestinal symptoms may be demonstrated, together with elevated temperatures and inflamed or involved mucus membranes. A frequent, and potentially severe, symptom that is associated with the disease is an extremely watery diarrhea which may persist for an extended period of time. The diarrhea may also be accompanied by indications of laminitis. In a significant number of cases, severe pain, and death are encountered. Thus, the disease represents both a veterinarian problem, and a potentially significant commercial loss.

Unlike many diseases of livestock, evidence is increasing that PHF is transmitted through the blood, probably via an insect vector, although no particular vector has been established. Thus, a frequent treatment for livestock, isolation of infected individuals until the disease has passed, simply won't work. It is difficult, practically impossible, to practice effective isolation in a large horse community sufficient to exclude the entry and departure of insect vectors.

Additionally, the fact that the disease is not transferred through casual contact, or through waste material, frustrates many commonly employed treatment/prevention steps.

Once identification of the disease and ehrlichial agent was made, many practitioners began administration of tetracycline for the treatment of PHF. This is the drug of choice in the treatment of canine ehrlichiosis. However, this method of treatment is not without its attendant pitfalls. Many concurrent Salmonella carriers will develop diarrhea following the use of tetracycline, thus causing the problem sought to be avoided. This may constitute 15% or more of the potential horse population. Further, in experimental trials, oxytetracycline, the particular drug of choice, was found not to prevent infection or successfully treat it, but rather, extend the incubation period, delaying onset of the disease. Additionally, as is well known, the administration of tetracycline can adversely affect acute equine enteritis present, or caused by, other organisms.

A further problem presented by treating PHF in conventional modes, including administration of tetracycline, is the possible persistence of the causitive agent. A related microbe, ehrlichia canis (the canine counterpart) can proliferate continuously and survive indefinitely in an immunologically competent animal. Robl, *Veterinary Medicine*, pages 49-58 (1985). Thus, there is a good likelihood that once-infected animals, subsequently treated with a masking drug, may remain walking carriers, capable of infecting many stall-mates, upon peaking of the next vector growth-cycle.

In view of all the problems associated with conventional treatment of the disease, the provision of an effective vaccine remains a compelling priority, one which has yet to be filled. Robl, supra.

Additionally, an assay which is as easy sa the ELISA assay currently available, but far more sensitive, is essential for control of the disease.

Preparation of the Vaccine

The active agent of the vaccine of this invention is deactivated, version of the causitive agent, *E. risticii*. The method as set forth below allows easy, preferably serial-passage, propagation, followed by "in-cell" deactivation, and subsequent isolation. Such a process has obvious advantages, in that deactivation of the active agent of the vaccine can be accomplished while the agent is present in its serial passage host. This avoids many problems encountered in conventional deactivation processes. In particular, this allows for chemical deactivation over an optimum time length, making it possible to maintain a high level of antigenicity in the causitive agent, to be employed as the active agent in the vaccine.

To secure inactivated *E. risticii* agents for use in a vaccine, commercially available mouse macrophage cell cultures are inoculated with *Ehrlichia risticii*, which may be subsequently serially passaged, if desired. An exemplary, but by no means limiting, mouse macrophage continuous cell culture that may be used in practicing this invention is P388D-1, obtained from the Naval Medical Research Institute, Bethesda, Md.

The infected culture produced was then treated, intact, with an amount of $\beta$-propiolactone, in a concentration effective to deactivate the agent, but preserve sufficient antigenicity to give rise to high titers of *E. risticii* antibody in vaccinated hosts. In actual practice, a range from about 0.1-0.5 has been demonstrated to be effective, with a preferred range being about 0.2-0.4%, by weight, resulting in a final concentration of about 0.2%.

Exposure to the $\beta$-propiolactone is continued, at room temperature, for a substantial length of time.

Again, the actual length of time exposure is practiced is a compromise between a desire to fully inactivate the agent, and to maintain sufficient antigenicity to induce high titers of antibodies in horses. In practice, an exposure value of about 40–75 hours, preferably 48–72 hours, at room temperature, has been found to be an optimum compromise.

Once exposed, all that remains is to isolate the deactivated or inactivated *E. risticii* from the mouse macrophage cell culture, and incorporate an effective amount in a pharmaceutically acceptable carrier.

Methods of isolation are well known to those of skill in the art, and do not constitute a central aspect of this invention. One principal method for isolation is centrifugation. The above-described culture, centrifuged at 5000 RPM, the supernatant thereafter centrifugal at 10,000 RPM, gives a confirmed cell pellet which may be resuspended to a 20-fold concentration. If the resuspended culture is sonicated for 30 seconds, 4 repetitions, sufficient isolation of the agent is achieved to allow preparation of effective vaccines.

When incorporating the agent in a pharmaceutically acceptable carrier, the route of administration must be taken into consideration. The vaccine of this invention may be administered by a variety of routes, including intradermal, intramuscular and subcutaneously. In general, any carrier commonly associated as acceptable with these methods of administration may be used. In particularly preferred examples, the carrier comprises an oil adjuvant, which is added to the centrifuged and isolated deactivated agent. Among adjuvants, Aralcel, in a concentration of about 1%–10%, preferably, 4–6%, by weight, can be favorably employed. This may be combined with other conventional emulsifiers, e.g., Tween 80 and supports, to provide a vaccine which is easily administered. The final step is to homogenize the mixed product.

Effective concentrations of the active agent are established through routine testing, according to well known protocols. This is particularly because the antigenicity of *E. risticii* may vary from sample to sample, and in density of infection of any given host culture, such as the mouse macrophage continuous cell culture described above. However, as a baseline, if the above-described mouse macrophage cell culture is ??? to a density of $6 \times 10^5$ cells per ml, and subsequently treated at a final concentration of $\beta$-propiolactone of 0.2%, for a period of 48–72 hours, followed by centrifugation at 5000 RPM, resuspension to a concentration 20 time that of acquired addition of Tween 80 at a final concentration of 5%, mixed with a mixture of Draketex 50 and Arlacel A (32:1) in 1:4 parts, IM injections of about 0.5–3 ml of the resulting vaccine, per 1000–1500 lbs. adult body weight, more preferably, 1–2 ml of the vaccine, have been demonstrated effective to provide a level of deactivated *E. risticii* antigen which will result in a significant measure of resistance to infection. Of course, prophylactic vaccination may be through a single administration, or, more preferably, in multiple administrations over time, to build-up and maintain an effective antibody titer.

It is particularly surprising that the vaccine produced according to the above-described process results in extremely high antibody titers in vaccinated horses, much higher than seen is a naturally infected animal. While the inventors do not wish to bound by this theory, it appears that the preservation of the high level of antigenicity according to the above-described process may be responsible for these extremely high titers, which, of course, confer an extra degree of protection on the vaccinated individual.

Assay

To prepare an unusually sensitive, high speed assay for *E. risticii* antibodies, human macrophage cell cultures, e.g., human histocyte lymphoma cultures, a particular example being U-937 of the ATCC, may be inoculated with *E. risticii* and propagated. Exemplary propagation media include RPMI 1640, which may be used alone or supplemented, e.g., with fetal bovine serum.

After centrifugation and pelletizing, the harvested cells are resuspended in a concentrate, e.g., 50-fold. These are then used to prepare a ELISA antigen pursuant to established techniques. The suspension prepared from the concentrated cells was in turn suspended over a renofin gradient and centrifuged. In the gradient, at least three bands are observed. The middle band, having a measured density of about 1.18–1.19, and specified as having a density of 1.182 g/ml, when employed in a conventional ELISA test, gives superior speed, accuracy and sensitivity.

Specifically, antigen-coated ELISA plates were treated with casein/BSA, serum, and an enzyme-labelled carrier, e.g., immunoglobulin, sequentially. Substrate was added, and after incubation at room temperature, absorbance at 405 nm was measured. Antibody titer was extremely high, allowing for quick and easy detection of the presence of the organisms, early in infection. Details of the process are set forth in Dutta et al, *Maryland Agricultural Experiment Station, Scientific Article No. A4292.*

EXAMPLES OF VACCINE EFFECTIVENESS

To demonstrate the inactivated nature of the agent of the vaccine of this invention, horses were inoculated with a vaccine preparation, through various routes of administration, with a vaccine preparation prepared according to the above description. The white blood cell count and conventional clinical signs were monitored for 28 days after vaccination. In all cases, the clinical signs were normal, and no marked variaton of white blood cell count was observed. It should be noted that a control vaccine, prepared from uninfected mouse macrophage cell culture, produced identical results.

To demonstrate the effectiveness of the vaccine of this invention, three different groups of horses, maintained under representative stabling conditions, were vaccinated. Members of each group received the effective, deactivated vaccine described above, with other members of the same group receiving the control vaccine, i.e., prepared from uninfected mouse macrophage cell cultures and unvaccinated control horses. Each group was challenged with *E. risticii,* through injection.

The vaccine conferred a large measure of protection on the horses so treated. In those individuals within each group that were vaccinated with the deactivated agent, in many cases, no symptoms of PHF were observed, and the only symptoms that were observed were mild (soft stools) and extremely transient. In contrast, the control individuals, vaccinated with the preparation from the uninfected culture, and unvaccinated control horses exhibited clinical signs of the disease.

To confirm the fact that it was indeed production of antibodies due to vaccination that was responsible for the protection conferred, antibody titers of vaccinated horses, both those receiving the vaccine prepared from deactivated, infected cell cultures and those receiving the control, were taken. While the titer values for the individuals receiving the vaccine prepared according to the above description were persistently high, increasing over the time period immediately after vaccination, the control individuals did not exhibit antibody titer over the same time period. A further control, on an unvaccinated individual in the same group, exhibited symptoms similar to the vaccinated control group. It should be noted that the protection conferred appears to be independent of the route of vaccination.

The above description of the vaccine, method of preparation, and method of administration of this invention is set forth in general terms, and illustrated with specific examples. It should be understood that the examples are illustrative only, and are not intended to limit the invention, the scope of which is outlined in general discussion, consistent with the claims set forth below. It will be therefore apparent to those of ordinary skill in the art that many changes and modifications can be made without departing from the spirit or the scope of the invention, as set forth herein.

What is claimed as new and desired to be secured by Letters patent of the United States is:

1. An antigen for use in an assay for the presence of *E. risticii* antibodies, comprising the product prepared from the process comprising:
    (a) culturing human macrophage cells inoculated with *E. risticii*,
    (b) harvesting, homogenizing and centrifuging cells suspended in a gradient, and
    (c) isolating and recovering the centrifuged band having a density in said gradient of 1.8–1.9 g/ml.

2. The antigen of claim 1, wherein said human macrophage cells are human histiocyte lymphoma cells.

3. The antigen of claim 1, modified by the attachment of an enzyme thereto, for use in an enzyme-linked immunosorbent assay.

4. A kit for conducting an enzyme-linked immunosorbent assay, comprising the antigen of claim 1 in a sealed container.

* * * * *